United States Patent [19]

Sanchez

[11] Patent Number: 4,477,449

[45] Date of Patent: Oct. 16, 1984

[54] CERTAIN 1,8-NAPHTHYRIDINE COMPOUNDS USEFUL AS ANTIBACTERIAL AGENTS

[75] Inventor: Joseph P. Sanchez, Canton, Mich.

[73] Assignee: Warner-Lambert Company, Morris Plains, N.J.

[21] Appl. No.: 468,836

[22] Filed: Mar. 1, 1983

Related U.S. Application Data

[63] Continuation-in-part of Ser. No. 369,689, Apr. 19, 1982, abandoned.

[51] Int. Cl.³ .................. A61K 31/435; C07D 471/04
[52] U.S. Cl. .................................... 424/246; 424/256; 544/58.2; 544/58.6; 546/123
[58] Field of Search .............. 546/123; 544/58.2, 58.6; 424/246, 256

[56] References Cited

PUBLICATIONS

Minami et al., Chem. Abstracts, vol. 84, 90178a, (1976).
Minami et al., Chem. Abstracts, vol. 84, 59558a, (1975).

*Primary Examiner*—Henry R. Jiles
*Assistant Examiner*—Bernard I. Dentz
*Attorney, Agent, or Firm*—Ronald A. Daignault

[57] ABSTRACT

Certain substituted 1,4-dihydro-4-oxo-7-(3-thiazolidinyl or 4-thiomorpholinyl)-1,8-naphthyridine-3-carboxylic acids and derivatives are disclosed as antibacterial agents.

9 Claims, No Drawings

CERTAIN 1,8-NAPHTHYRIDINE COMPOUNDS USEFUL AS ANTIBACTERIAL AGENTS

CROSS REFERENCE TO RELATED APPLICATION

This is a continuation-in-part of U.S. Ser. No. 369,689 filed Apr. 19, 1982, now abandoned.

BACKGROUND OF THE INVENTION

European Patent Application No. 80 40 1369, Publication Number 027,752, published Apr. 29, 1981, discloses certain substituted 7-(3-amino-1-pyrrolidnyl)-1-ethyl-6-fluoro-1,4-dihydro-4-oxo-1,8-naphthyridine-3-carboxylic acids having the general formula:

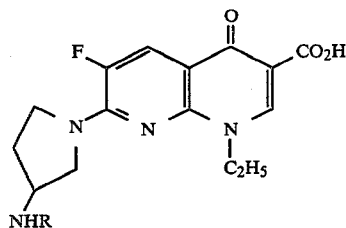

The compounds are disclosed to have antibacterial activity.

SUMMARY OF THE INVENTION

The invention sought to be patented in a generic chemical compound aspect is a compound having the structural formula I

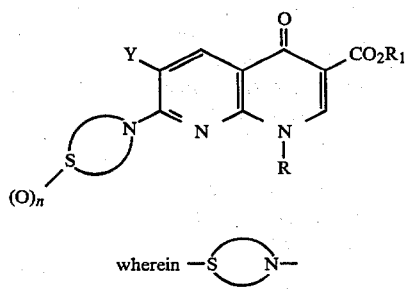

wherein $-S\underset{}{\overset{}{\diagup}}N-$ is thiazolidine or thiomorpholine; R is alkyl having from one to four carbon atoms, vinyl or haloalkyl having from two to four carbon atoms; Y is hydrogen or fluorine; n is 0, 1, or 2; $R_1$ is hydrogen, alkyl having from one to six carbon atoms or a cation derived from a pharmaceutically acceptable metal or amine; and the pharmaceutically acceptable salts thereof.

The invention sought to be patented in its first subgeneric chemical compound aspect is a compound having structural formula I wherein Y is fluorine and the pharmaceutically acceptable salts thereof.

The invention sought to be patented in its second subgeneric chemical compound aspect is a compound having the structural formula I wherein R is $C_2H_5$ and the pharmaceutically acceptable salts thereof.

The invention sought to be patented in its third subgeneric chemical compound aspect is a compound having the structural formula I wherein R is $C_2H_5$, Y is fluorine, and the pharmaceutically acceptable salts thereof.

The invention sought to be patented in its fourth subgeneric chemical compound aspect is a compound having the structural formula I wherein R is $C_2H_5$, Y is hydrogen and the pharmaceutically acceptable salts thereof.

The invention sought to be patented as specific chemical compounds are the compounds having the names: 1-ethyl-6-fluoro-1,4-dihydro-4-oxo-7-(3-thiazolidinyl)-1,8-naphthyridine-3-carboxylic acid; 1-ethyl-6-fluoro-1,4-dihydro-4-oxo-7-(3-thiazolidinyl)-1,8-naphthyridine-3-carboxylic acid, S-oxide; 1-ethyl-6-fluoro-1,4-dihydro-4-oxo-7-(3-thiazolidinyl)-1,8-naphthyridine-3-carboxylic acid, S, S-dioxide; 1-ethyl-6-fluoro-1,4-dihydro-4-oxo-7-(4-thiomorpholinyl)-1,8-naphthyridine-3-carboxylic acid, and the pharmaceutically acceptable salts thereof.

The invention sought to be patented in a generic chemical process aspect is a process for preparing a compound having the structural formula I which comprises reacting a compound having the structural formula II

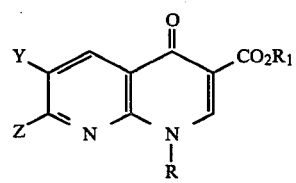

wherein R, $R_1$, and Y are defined above and Z is chlorine or bromine, with thiazolidine or thiomorpholine to obtain the compound of formula I wherein n is 0 and if desired oxidizing the thus produced compound to produce the corresponding compounds of formula I wherein n is 1 or 2.

The invention sought to be patented in a generic pharmaceutical composition aspect is a pharmaceutical composition comprising a compound having structural formula I and the pharmaceutically acceptable salts thereof in combination with a pharmaceutically acceptable carrier.

The invention sought to be patented in a pharmaceutical method aspect is a method for treating microbial infections in a mammal which comprises administering a sufficient amount of the above defined pharmaceutical composition to a mammal in need thereof.

DESCRIPTION OF THE PREFERRED EMBODIMENTS

The compounds of the invention wherein n is 0 are readily prepared by reacting a compound having the structural formula II

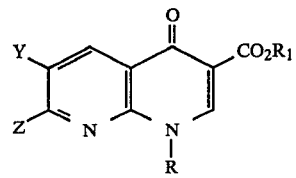

wherein R is $C_2H_5$ or $C_2H_3$; Y is hydrogen or fluorine; $R_1$ is hydrogen, alkyl having from one to six carbon atoms or a cation derived from a pharmaceutically acceptable metal or amine, and Z is chlorine or bromine with thiazolidine or thiomorpholine.

This reaction proceeds efficiently in a non-reactive solvent such as dimethylformamide in the presence of a hydrogen halide acceptor such as a tertiary amine preferably triethylamine, and the like. Other hydrogen halide acceptors such as potassium carbonate may also be utilized.

The compounds of formula I wherein n is 0 may be converted to the corresponding compounds wherein n is 1 or 2 by methods known to those skilled in the art. The compounds of formula I wherein n is 1 may also be converted to the corresponding compounds wherein n is 2 by known methods.

For example, treatment of a compound of formula I wherein n is 0 with aqueous sodium metaperiodate or with one equivalent of 30% hydrogen peroxide will produce the corresponding compound of formula I wherein n is 1. Treatment of a compound of formula I wherein n is 0, with two equivalents of 30% hydrogen peroxide will produce the corresponding compound of formula I wherein n is 2. Treatment of a compound of formula I wherein n is 1 with potassium permanganate or one equivalent of 30% hydrogen peroxide will produce the corresponding compound of formula I wherein n is 2.

The compounds of formula II may be prepared by methods described in European Patent Application 80 40 1369 by obvious variations thereof.

The compounds of the invention display antibacterial activity when tested by the microtitration dilution method as described in Heifetz et al, Antimicr. Agents and Chemoth., 6, 124 (1974), which is incorporated herein by reference.

By use of the above referenced method the following minimum inhibitory concentration values (MICs in μg/ml) were obtained for representative compounds of formula I.

|  | Ex. 1 | Ex. 2 | Ex. 3 | Ex. 4 |
| --- | --- | --- | --- | --- |
| *Entero. cloacae* MA2646 | 0.4 | 0.8 | 1.6 | 1.6 |
| *Esch. coli* Vogel | 0.1 | 0.2 | 0.8 | 0.2 |
| *Klebs. pneumo* MGH-2 | 0.4 | 1.6 | 3.1 | 0.8 |
| *Prot. rettgeri* M1771 | 0.4 | 0.8 | 6.3 | 6.3 |
| *Pseudo aerug.* UI-18 | 1.6 | 1.6 | 2.5 | 6.3 |
| *Staph. aureus* H228 | 0.05 | 1.6 | 3.1 | ≦0.1 |
| *Staph. aureus* UC76 | 0.025 | 0.4 | 0.8 | ≦0.1 |
| *Strep. faecalis* MGH-2 | 0.2 | 12.5 | 25 | 1.6 |
| *Strep. pneumo.* SV-1 | 1.6 | 100 | >100 | 25 |
| *Strep. pyog.* C-203 | 1.6 | 50 | >100 | 50 |

The compounds of the invention form pharmaceutically acceptable salts with organic and inorganic bases. Examples of suitable bases for salt formation are sodium hydroxide, potassium hydroxide, sodium carbonate, potassium carbonate, sodium bicarbonate, triethylamine, ammonia, morpholine, and the like. The salts are prepared by contacting the free form of the compound with an equivalent amount of the desired base in the conventional manner. The free forms may be regenerated by treating the salt form with an acid. For example, dilute aqueous acid solutions may be utilized to regenerate the free form from a respective salt. Dilute aqueous hydrochloric acid is suitable for this purpose. The free forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups contemplated by the invention comprise both straight and branched carbon chains of from one to four carbon atoms. Representative of such groups are methyl, ethyl, propyl, isopropyl, butyl, isobutyl, sec-butyl or t-butyl.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-difluoroethyl, β, β-dichloroethyl, β-fluoropropyl, β-chloropropyl, β-fluoro-2-propyl, β-chloro-2-propyl, γ-fluorobutyl, γ-chlorobutyl, and the like.

The compounds of the invention can be prepared and administered in a wide variety of oral and parenteral dosage forms. It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as antibacterial agents, the compounds utilized in the pharmaceutical method of this invention are administered at the initial dosage of about 0.1 mg to about 100 mg per kilogram daily. A daily dose range of about 0.5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting example illustrates the inventor's preferred methods for preparing the compounds of the invention.

EXAMPLE 1

1-Ethyl-6-fluoro-1,4-dihydro-4-oxo-7-(3-thiazolidinyl)-1,8-naphthyridine-3-carboxylic acid A solution of 1.0 g (3.7 mmol) of 7-chloro-1,4-dihydro-1-ethyl-6-fluoro-4-oxo-1,8-naphthyridine-3-carboxylic acid, 0.8 g (8.0 mmol) of triethylamine, 1.1 g (12.0 mmol) of 97% thiazolidine in 30 ml of N,N-dimethylformamide was stirred at room temperature for 18 hours. The solvent was removed at reduced pressure and the residue dissolved in water using 1.0N sodium hydroxide to adjust to pH 12.0. The solution was filtered to remove a trace of insoluble material and the filtrate was acidified to pH=3.0 with 6.0N hydrochloric acid. The precipitate was removed by filtration, washed with water and the wet filter cake recrystallized from ethanol clarifying with charcoal to give 0.6 g of 1-ethyl-6-fluoro-1,4-dihydro-4-oxo-7(3-thiazolidinyl)-1,8-naphthyridine-3-carboxylic acid; mp 288°–289° C.

EXAMPLE 2

1-Ethyl-6-fluoro-1,4-dihydro-4-oxo-7-(3-thiazolidinyl)-1,8-naphthyridine-3-carboxylic acid, S-oxide To a suspension of 0.34 g (1.05 mmol) of 1-ethyl-6-fluoro-1,4-dihydro-4-oxo-7-(3-thiazolidinyl)-1,8-naphthyridine-3-carboxylic acid in 1.2 ml of trifluoroacetic acid was added 0.26 ml (1.05 mmol) of 4.0M peroxytrifluoroacetic acid maintaining the temperature at 0° C. The reaction was stirred at 0° C. for two hours and then at room temperature for 18 hours. The reaction was filtered and the precipitate was triturated with ethanol to give 0.16 g of 1-ethyl-6-fluoro-1,4-dihydro-4-oxo-7-(3-thiazolidinyl)1,8-naphthyridine-3-carboxylic acid, S oxide; mp 283°–285° C.

EXAMPLE 3

1-Ethyl-6-fluoro-1,4-dihydro-4-oxo-7-(3-thiazolidinyl)-1,8-naphthyridine-3-carboxylic acid, S,S-dioxide A suspension of 0.48 g (1.5 mmol) of 1-ethyl-6-fluoro-1,4-dihydro-4-oxo-7-(3-thiazolidinyl)-1,8-naphthyridine-3-carboxylic acid and 0.69 g (3.2 mmol) of 80% meta-chloroperoxybenzoic acid in 100 ml of dichloromethane was stirred at room temperature for 48 hours. The solvent was removed in vacuo and the residue was washed with ether and dissolved in 1.0N sodium hydroxide to pH 12.0. The hazy solution was filtered through a fiber glass pad to clarify and was then acidified to pH 2.0 with 6.0N hydrochloric acid. The resulting precipitate was removed by filtration, washed successively with water, ethanol, and ether and then dried in vacuo. The dried solid was then recrystallized from aqueous ethanol to give 170 mg of 1-ethyl-6-fluoro-1,4-dihydro-4-oxo-7-(3-thiazolidinyl)-1,8-naphthyridine-3-carboxylic acid, S,S-dioxide; mp 268°–270°.

EXAMPLE 4

1-Ethyl-6-fluoro-1,4-dihydro-4-oxo-7-(4-thiomorpholinyl)-1,8-naphthyridine-3-carboxylic acid A suspension of 0.271 g (1.0 mmol) of 7-chloro-1,4-dihydro-1-ethyl-6-fluoro-4-oxo,1,8-naphthyridine-3-carboxylic acid, 0.316 g (3.0 mmol) of thiomorpholine and 30 ml of acetonitrile was heated at reflux for 18 hours. The solvent was removed in vacuo and the residue was recrystallized from aqueous ethanol to give 130 mg of 1-ethyl-6-fluoro-1,4-dihydro-4-oxo-7-(4-thiomorpholinyl)-1,8-naphthyridine-3-carboxylic acid; mp 241°–243° C.

I claim:

1. A compound having the structural formula:

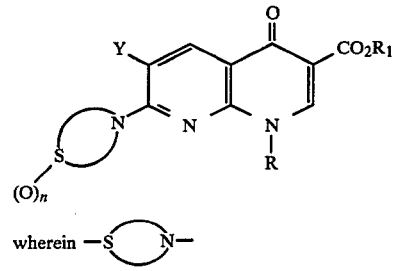

wherein $-S\underset{}{\bigcirc}N-$ is thiazolidine or thiomorpholine; R is alkyl having from one to four carbon atoms, vinyl or haloalkyl having from two to four carbon atoms; Y is hydrogen or fluorine; n is 0, 1, or 2; $R_1$ is hydrogen, alkyl from one to six carbon atoms or a cation derived from a pharmaceutically acceptable metal or amine, and the pharmaceutically acceptable salts thereof.

2. The compounds defined in claim 1 wherein Y is fluorine and the pharmaceutically acceptable salts thereof.

3. The compounds defined in claim 2 wherein R is $C_2H_5$ and the pharmaceutically acceptable salts thereof.

4. The compound defined in claim 1 having the name 1-ethyl-6-fluoro-1,4-dihydro-4-oxo-7-(3-thiazolidinyl)-1,8-naphthyridine-3-carboxylic acid and the pharmaceutically acceptable salts thereof.

5. The compound defined in claim 1 having the name 1-ethyl-6-fluoro-1,4-dihydro-4-oxo-7-(3-thiazolidinyl)-

1,8-naphthyridine-3-carboxylic acid, S-oxide and the pharmaceutically acceptable salts thereof.

6. The compound defined in claim 1 having the name 1-ethyl-6-fluoro-1,4-dihydro-4-oxo-7-(3-thiazolidinyl)-1,8-naphthyridine-3-carboxylic acid, S,S dioxide and the pharmaceutically acceptable salts thereof.

7. The compound defined in claim 1 having the name 1-ethyl-6-fluoro-1,4-dihydro-4-oxo-7-(4-thiomorpholinyl)-1,8-naphthyridine-3-carboxylic acid and the pharmaceutically acceptable salts thereof.

8. A pharmaceutical composition comprising an antibacterially effective amount of a compound as defined in claim 1 and the pharmaceutically acceptable salts thereof in combination with a pharmaceutically acceptable carrier.

9. A method for treating microbial infections in a mammal which comprises administering a pharmaceutical composition defined in claim 8 to a mammal in need thereof.

* * * * *